(12) United States Patent
Zhao et al.

(10) Patent No.: US 8,349,006 B2
(45) Date of Patent: Jan. 8, 2013

(54) GLARE REDUCING ROUGH SURFACES

(75) Inventors: Huawei Zhao, Irvine, CA (US); Nguyen Q Nguyen, Costa Mesa, CA (US); Duc Tran, Irvine, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 13/224,822

(22) Filed: Sep. 2, 2011

(65) Prior Publication Data

US 2012/0032363 A1    Feb. 9, 2012

Related U.S. Application Data

(60) Continuation of application No. 12/875,434, filed on Sep. 3, 2010, now Pat. No. 8,012,203, which is a continuation of application No. 12/163,912, filed on Jun. 27, 2008, now Pat. No. 7,811,319, which is a division of application No. 10/638,036, filed on Aug. 8, 2003, now abandoned.

(51) Int. Cl.
*A61F 2/16* (2006.01)
(52) U.S. Cl. ..................................... 623/6.17
(58) Field of Classification Search .............. None
See application file for complete search history.

(56) References Cited

U.S. PATENT DOCUMENTS

| | | | |
|---|---|---|---|
| 4,676,791 | A | 6/1987 | LeMaster et al. |
| 5,054,905 | A | 10/1991 | Cohen |
| 5,281,294 | A | 1/1994 | Freeman et al. |
| 5,405,385 | A | 4/1995 | Heimke et al. |
| 5,549,670 | A | 8/1996 | Young et al. |
| 6,129,759 | A | 10/2000 | Chambers |
| 6,162,249 | A | 12/2000 | Deacon et al. |
| 6,264,693 | B1 | 7/2001 | Ross |
| 6,283,974 | B1 | 9/2001 | Alexander |
| 6,468,306 | B1 | 10/2002 | Paul et al. |
| 6,790,873 | B2 | 9/2004 | Tomono et al. |
| 6,884,262 | B2 | 4/2005 | Brady et al. |
| 2005/0177230 | A1 | 8/2005 | Young |
| 2006/0004396 | A1 | 1/2006 | Easley et al. |
| 2009/0137971 | A1 | 5/2009 | Akahoshi |

FOREIGN PATENT DOCUMENTS

EP    246754 A1    11/1987

*Primary Examiner* — David H Willse
*Assistant Examiner* — Javier Blanco
(74) *Attorney, Agent, or Firm* — Abbott Medical Optics Inc.

(57) ABSTRACT

An intraocular lens for insertion into a capsular bag in order to focus incoming light toward a retina and process for manufacturing thereof along with concomitant reduced glare and improved vision provides for a center lens portion of a lens for focusing incoming light toward the retina and the surrounding lens portion for mounting the lens within the capsular bag. A surface roughness disposed on the surrounding lens portion is provided for reducing the glare due to non-focused light directed toward the retina from the intraocular lens with the roughness having a roughness level of between about Ra 45 and about Ra 350.

4 Claims, 8 Drawing Sheets

GLARE REDUCING ROUGH SURFACES

RELATED APPLICATIONS

This application is a continuation application of, and claims priority to, application Ser. No. 12/875,434, filed Sep. 3, 2010 now U.S. Pat. No. 8,012,203 issued on Sep. 6, 2011, which is a continuation application of, and claims priority to, application Ser. No. 12/163,912, filed Jun. 27, 2008, now U.S. Pat. No. 7,811,319 issued on Oct. 12, 2010, which is a divisional of, and claims prioity to, application Ser. No. 10/638,036, filed Aug. 8, 2003, now abandoned, all of which are herein incorporated by reference in their entirety.

The present invention generally relates to apparatus and methods for improving vision of an eye with a cataractic lens. More particularly, the present invention relates to an intraocular lens for insertion into a capsular bag in order to focus incoming light toward a retina and still more particularly relates to a process of fabricating an intraocular lens, which includes roughening portions of the lens in order to reduce glare due to non-focused light directed toward the retina from the intraocular lens.

A typical intraocular lens (IOL) is formed from a suitable synthetic material, such as silicone, and shaped for insertion into an eye. The IOL may be utilized in place of, or, in addition to, the natural lens of the eye to correct vision. Often the IOL replaces the natural lens in the capsular bag after removal of the natural lens.

A number of different types of IOL's have been developed for correcting various types of vision disorders.

While most IOL's are suitable for correcting visual disorders, they also typically cause the recipient to experience undesirable side effects commonly referred to as "glare".

This glare has been described as an arc, or pattern, with concentrated intensity and high local contrast. That is, the glare is a brightened pattern which is easily distinguished by the recipient over other images projected onto a retina by the lens. Accordingly, to reduce this glare perception, both the glare pattern intensity and the local contrast must be reduced below vision recognizable or perception thresholds.

Often, these glare effects which may be perceived as haloes, arcs of light, flashing of light, as well as shadows are often caused by peripheral edges of the implanted IOL.

Specifically designed IOL edges have proved to be very effective on reducing edge glare phenomenon. Rounded edges have proved to be able to reduce glare perception by breaking the glare light concentration of a specific pattern and thereby decreasing the glare pattern average intensity and local contrast.

Of particular importance in that regard is disclosed in U.S. Pat. No. 6,468,306 to Paul, Brady, and Deacon. This patent is incorporated in its entirety into the present application by this specific reference thereto. This design hereinafter may be referred to as OptiEDGE (Advanced Medical Optics, Santa Ana, Calif.) has been successfully designed to reduce edge glare. For instance, a rounded transition surface on the anterior side of the peripheral edge diffuses the intensity of reflected light, or a particular arrangement of straight edge surfaces refracts the light so as not to reflect, or does not reflect at all.

It has also been found and reported in U.S. Pat. No. 6,162,249 that the use of frosting, or roughening areas of the IOL can reduce glare. In this regard, the basic concept is the use of a roughened surface to avoid internally reflecting rays from causing the unwanted visual glare.

The present invention is directed to a process for fabricating a surface on an intraocular lens to provide optimum roughening thereof to produce a random scattering surface finish. In that regard, the present invention also encompasses an intraocular lens utilizing that the surface, a method for reducing glare from an intraocular lens onto a retina and ultimately a method for improving vision of an eye.

SUMMARY OF THE INVENTION

An intraocular, lens in accordance with the present invention for insertion into a capsular bag, is provided for focusing incoming light toward a retina. The lens generally includes a center lens portion for focusing incoming light toward the retina and a surrounding lens portion for mounting the lens within the capsular bag.

A surface roughness disposed on the surrounding lens portion is provided for reducing glare due to non-focused light directed toward the retina from the intraocular lens. The surface roughness has roughness level of between about Ra 45 and about Ra 350.

In accordance with an embodiment of the present invention, the surface roughness is produced by Electrical Discharge Machining and the surrounding lens portion comprises silicone.

More particularly, it has been found that a roughness level of about Ra 180 is particularly suitable for reducing glare. The surface roughness may be disposed on anterior and posterior surfaces of the surrounding lens portion and selected portions having the provided surface roughness may include at least one haptic for fixing a lens within the capsular bag.

Preferably, the surrounding lens portion includes a peripheral edge surface intersecting at least one of the anterior and a posterior surface to form a corner therebetween and a surface roughness, or frosting, is disposed on the anterior and posterior surfaces other than the corner.

Also in accordance with the present invention, a process for fabricating a surface on an intraocular lens is provided with the process comprising roughening a smooth lens surface by Electrical Discharge Machining to a roughness level of between about Ra 45 and about Re 350.

In addition, the present invention provides for a process of fabricating an intraocular lens which includes providing a blank lens having a center lens portion and a surrounding lens portion and roughening the surrounding lens portion by electrical discharge machining to a roughness level of between about Ra 45 and about Ra 350.

Ultimately, the present invention provides a method for improving vision of an eye with a cataractic lens with the method including the steps of removing a cataractic lens from the lens capsule and inserting an intraocular lens into the capsule with the intraocular lens including a center lens portion for focusing incoming light toward the retina, a surrounding lens portion for mounting the lens within the capsular bag and a surface roughness disposed on the surrounding lens portion for reducing glare due to non-focused light directed toward the retina from the intraocular lens. The surface roughness has a roughness level of between about Ra 45 and about Ra 350.

Likewise, the present invention comprises using the method taught for phakic lenses and contemplates all of the disclosed steps with removal of the lens or during a "clear lens-ectomy" or procedure without removal of a cataractous or "cloudy" lens.

BRIEF DESCRIPTION OF THE DRAWINGS

The advantages and features of the present invention will be better understood by the following description when considered in conjunction with the accompanying drawings in which.

DETAILED DESCRIPTION

Figures 1A, 1B, 2:
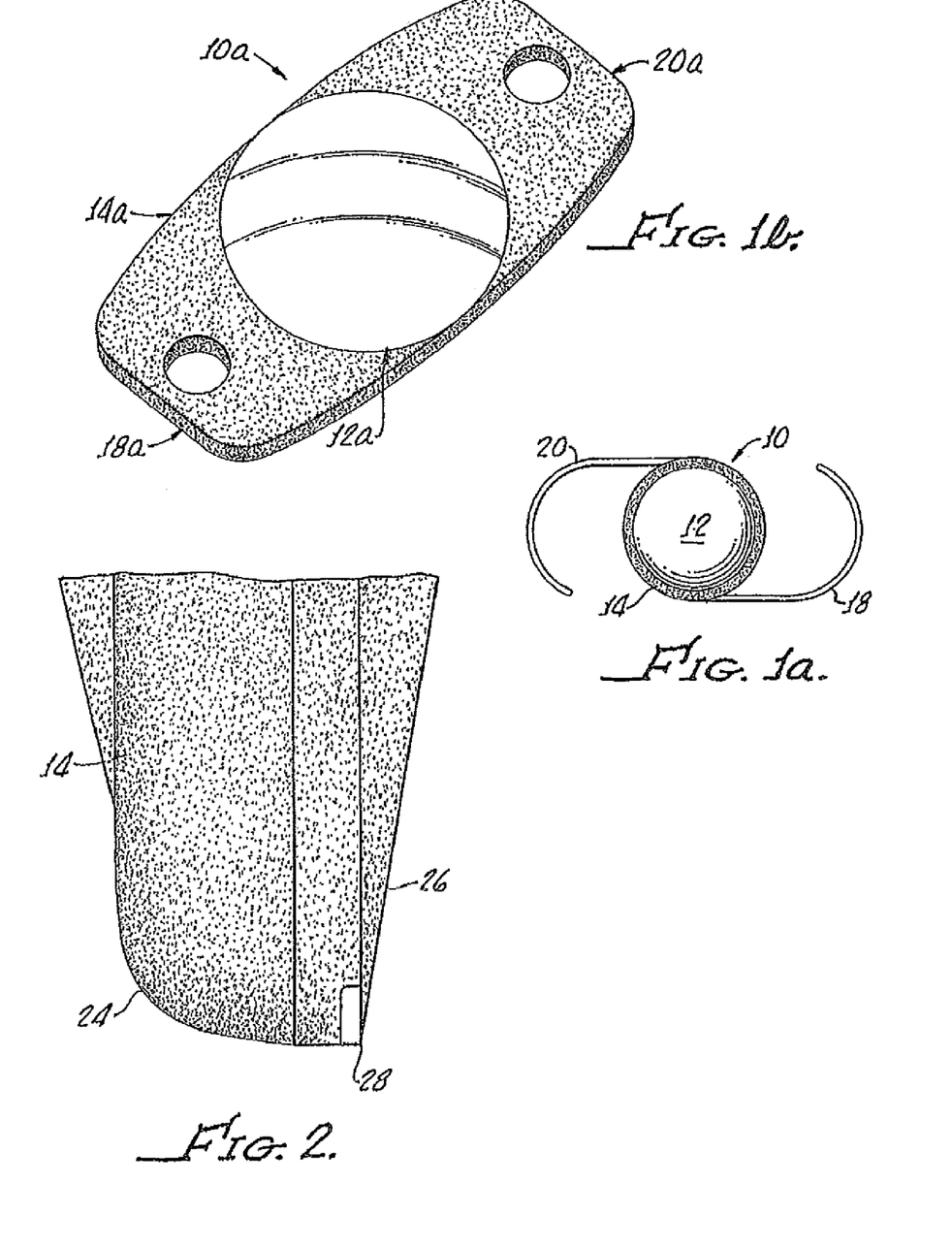
FIGS. 1a and 1b are representations of intraocular lenses which may be produced in accordance with the present invention having a center lens portion for focusing incoming light toward a retina (not shown in FIG. 1) and a surrounding lens portion for mounting a lens within a capsular bag (not shown in FIG. 1)
FIG. 2 is an enlarged end view of the surrounding lens portion shown in FIG. 1 with a surface roughness disposed thereon.

With reference to FIGS. 1a and 1b, there is illustrated intraocular lenses (IOLS) 10, 10a having center portions 12, 12a for focusing incoming light toward the retina of an eye (not shown in FIG. 1) and a surrounding lens portion 14, 14a which may include fixation members, or haptics, 18, 18a, 20, 20a for fixing the lens 10, 10a within a capsular bag (not shown in FIG. 1) in a conventional manner. The lenses 10, 10a may be formed from any suitable material such as, for example, silicone, poly(methylmetharylate) or other solid elastically deformable materials formed from functional groups such as, but not limited to vinylic, acrylic, methacrylic groups, i.e. hybrid material.

As more clearly shown in FIG. 2, a surface roughness is disposed on the surrounding lens portion anterior surface 24 for reducing glare due to non-focused light directed toward the retina from the intraocular lens, as will be hereinafter discussed in greater detail. A posterior surface 26 may also be roughened. As illustrated surrounding lens portion 14 may include a corner 28 and no surface roughening is applied thereto.

The surface roughness has a roughness level of between about Ra 45 and about Ra 350 and preferably about Ra 180.

Surface roughness is the arithmetic mean roughness value which is calculated from the integral of the absolute value of peak or valley with respect to a centerline, according to standard methods.

Figure 3:
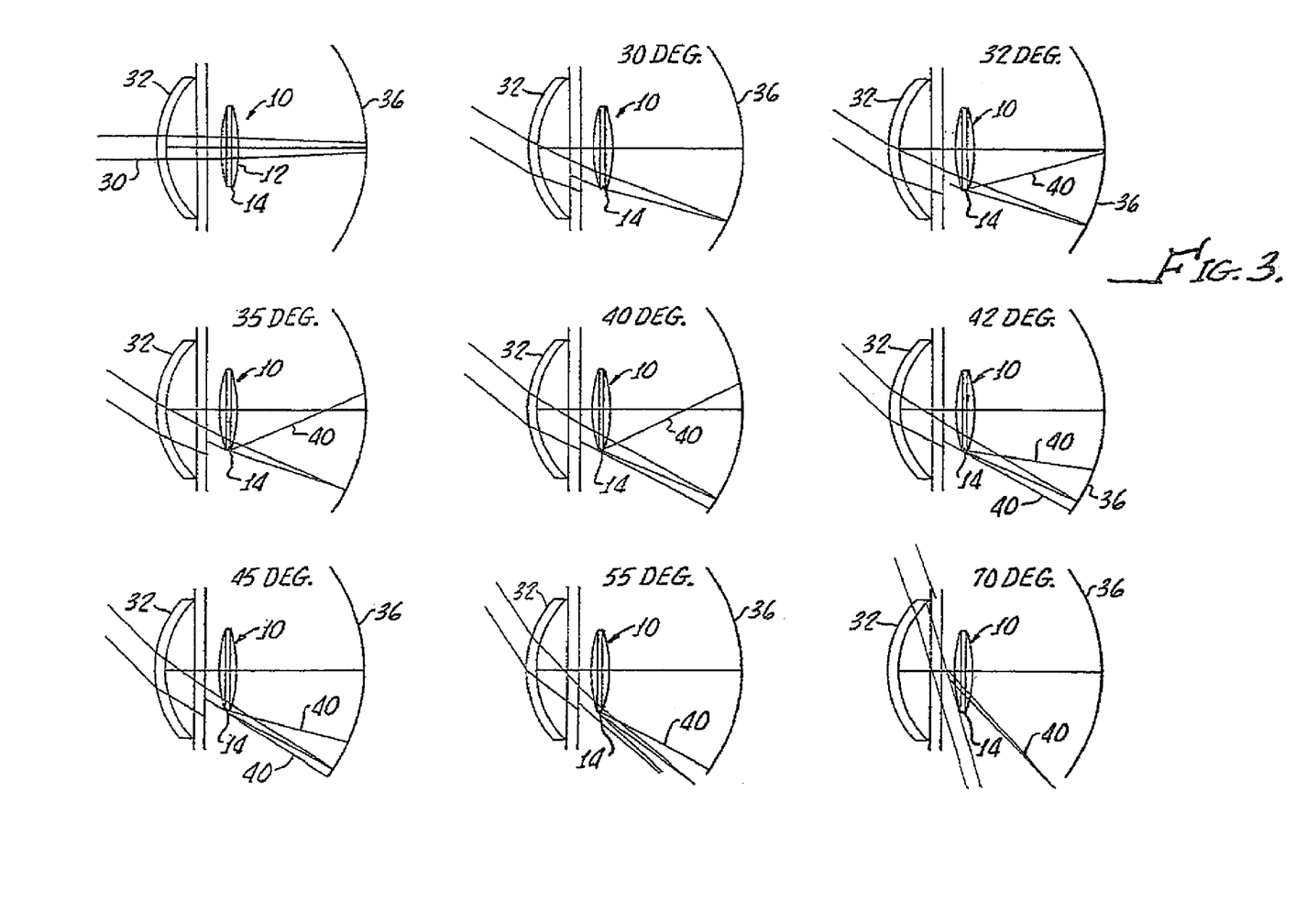
FIG. 3 is a diagram of light at incident angles from 0 to 70° showing passage through a cornea/lens and corresponding edge glares produced.

With reference to FIG. 3, there is illustrated an intraocular lens 10 for focusing incoming light through a cornea 32 toward a retina 36 as well as glare caused by non-focused light 40 directed toward the retina 36 from the intraocular lens 10 at various incident angles of the incoming light 30, namely 30°-70°.

Figure 4:
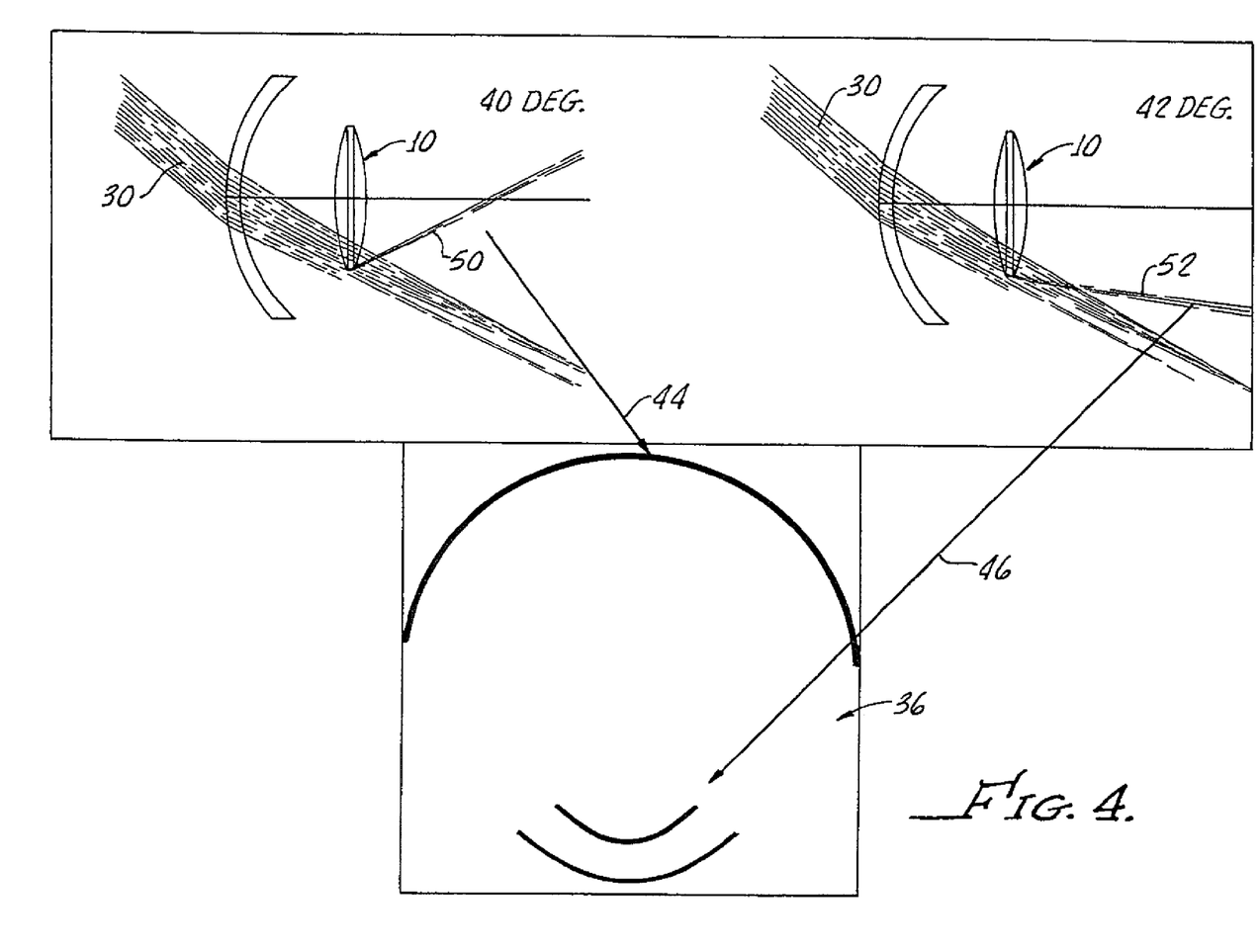
FIG. 4 is a diagram illustrating the occurrence of reflected and transmitted edge glare and resulting images on a retina.

FIG. 4 illustrates the glare patterns 44; 46 on the retina 36 at a 40° incident angle of incoming light. Reflected light, illustrated by the line 50, causes an arcuate pattern curved toward the source of light while incoming light at 42° incident angle produces non-focused light, indicated by the line 52, due to transmitted light which produces the glare pattern 46 which is curved away from the source.

Figure 5:
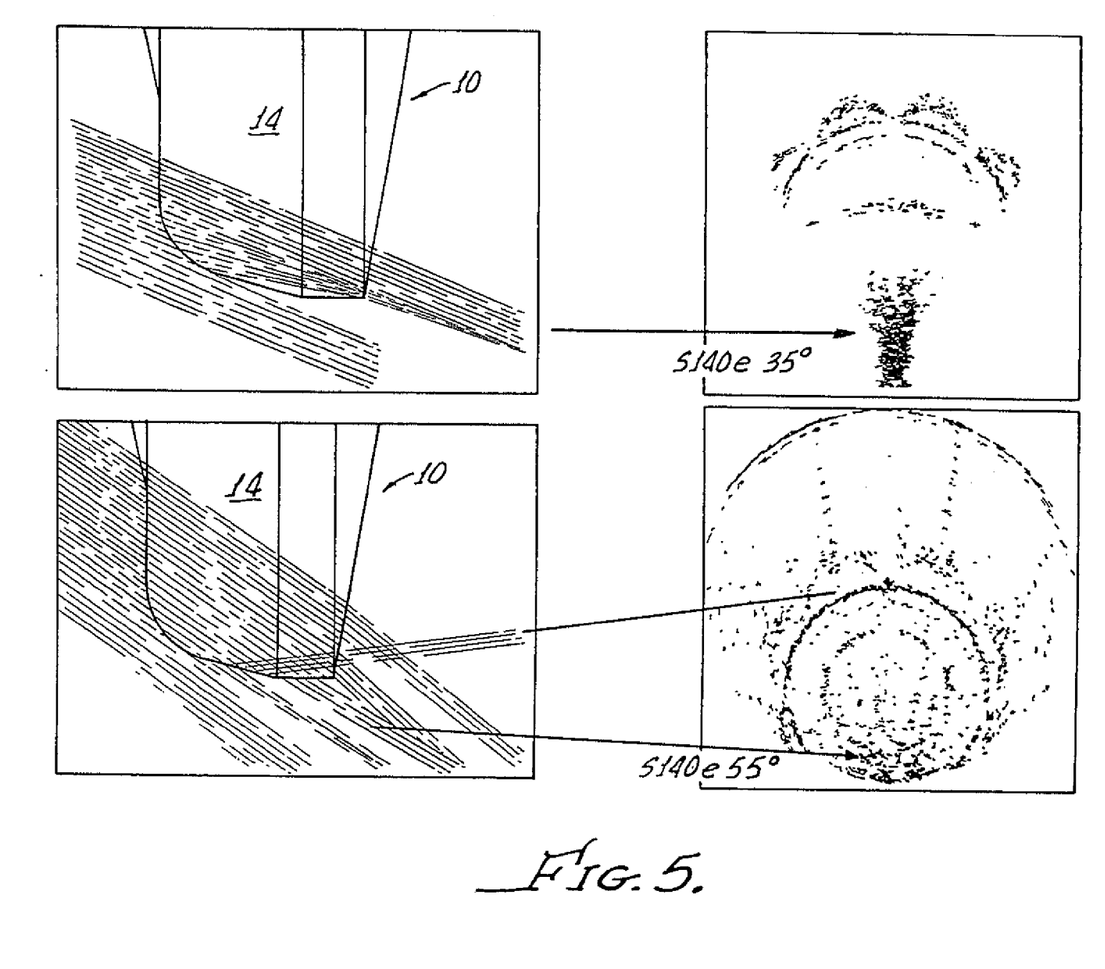
FIG. 5 is a diagram illustrating the surrounding the lens portion shown in FIG. 2 and resulting glare from incident light at 35° and 55° incident angle.

FIG. 5 illustrates simulated glare from the lens 10 without the surface roughness at incident light angles of 35° and 55° on an S140e lens (Advanced Medical Optics, Santa Ana, Calif.).

The present invention provides for a roughened surface 24 on the lens-surrounding portion 14 as shown in FIG. 2 to provide a random scattering surface. With a random scattering surface, the glare patterns are effectively reduced or eliminated, that is, glare is not perceived due not only to reduction in glare intensity but also in a reduction of glare contrast. In other words, random light scattering provides a uniform contrast level on the retina which does not include contrasted glare patterns as hereinbefore discussed.

A discussion of random scattering is useful in understanding the present invention. A random scattering surface can be modeled at the surface with uniform scattering in all directions in an ideal case such as a Lambertian Scattering Surface shown in FIG. 6.

Figure 6:
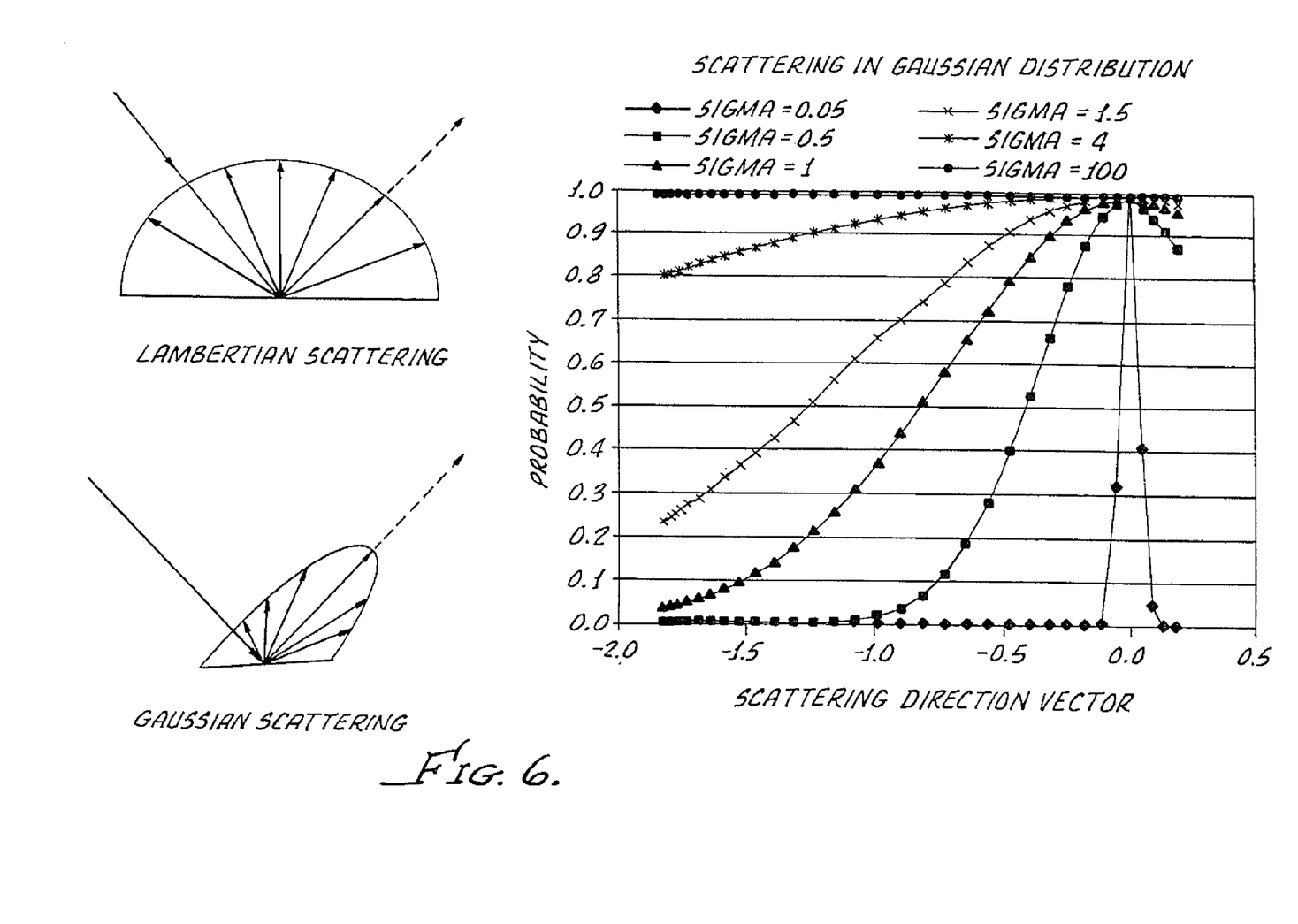
FIG. 6 is an illustration of surface scattering with different scattering probability models.

FIG. 6 shows an illustration of the probability distribution of such a scattering model. However, a practical surface usually is more accurately modeled as a surface that scatters light in Gaussian distribution relative to the spectacular ray which is either the reflective ray or transmitted ray.

FIG. 6 also gives the probability curve for Gaussian scattering distribution. When the distribution width sigma is very large (that is >1) the surface is close to a uniform scattering surface, whereas when the distribution width sigma is very narrow (<0.1) the surface is close to an optical surface.

The distribution amplitude represents a scattering level at a specific scattering direction. It is the ratio of all energy associated to the scattered rays to the total energy associated to all reflected or transmitted rays. The larger the spattering level the more energy associated with the scattering ray.

Figure 7:
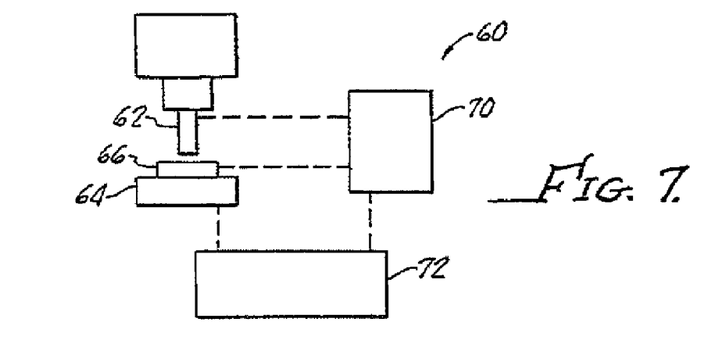
FIG. 7 is a schematic representation of Electrical Discharge Machine apparatus for producing the surface roughness.

The intraocular lens 10 and the surface roughness, or frosting, 24 provided thereon is fabricated by providing a blank lens, preferably silicone, having the center lens portion 12 and surrounding lens portion 14 and thereafter roughening the surrounding lens portion 14 by Electrical Discharge Machining utilizing apparatus 60 diagramed in FIG. 7.

Generally, the Electronic Discharge Machining apparatus 60 includes an electrode tool 62, a slide table 64, and a work piece 66 for supporting the intraocular lens 10 (not shown in FIG. 7). A pulse generator 70 provides a voltage differential between the electrode tool 62 and work piece 66 which is driven by a programmable circuit 72.

In a simplistic description of one mode of operation, the lens 10, 10*a* is disposed on the work piece and the pulsed generator and slide table manipulated to provide the roughness 24 on the lens 10, 10*a* to a specified surface roughness Ra. As a specific example a program usable on an Electrical Discharge Machine available at Porex Medical Products in Ontario, Calif. is set forth in Table 1 for providing a Ra 180 surface on silicone lenses 10, 10*a* as indicated by the surface 24 shown in FIG. 2.

Figure 8:
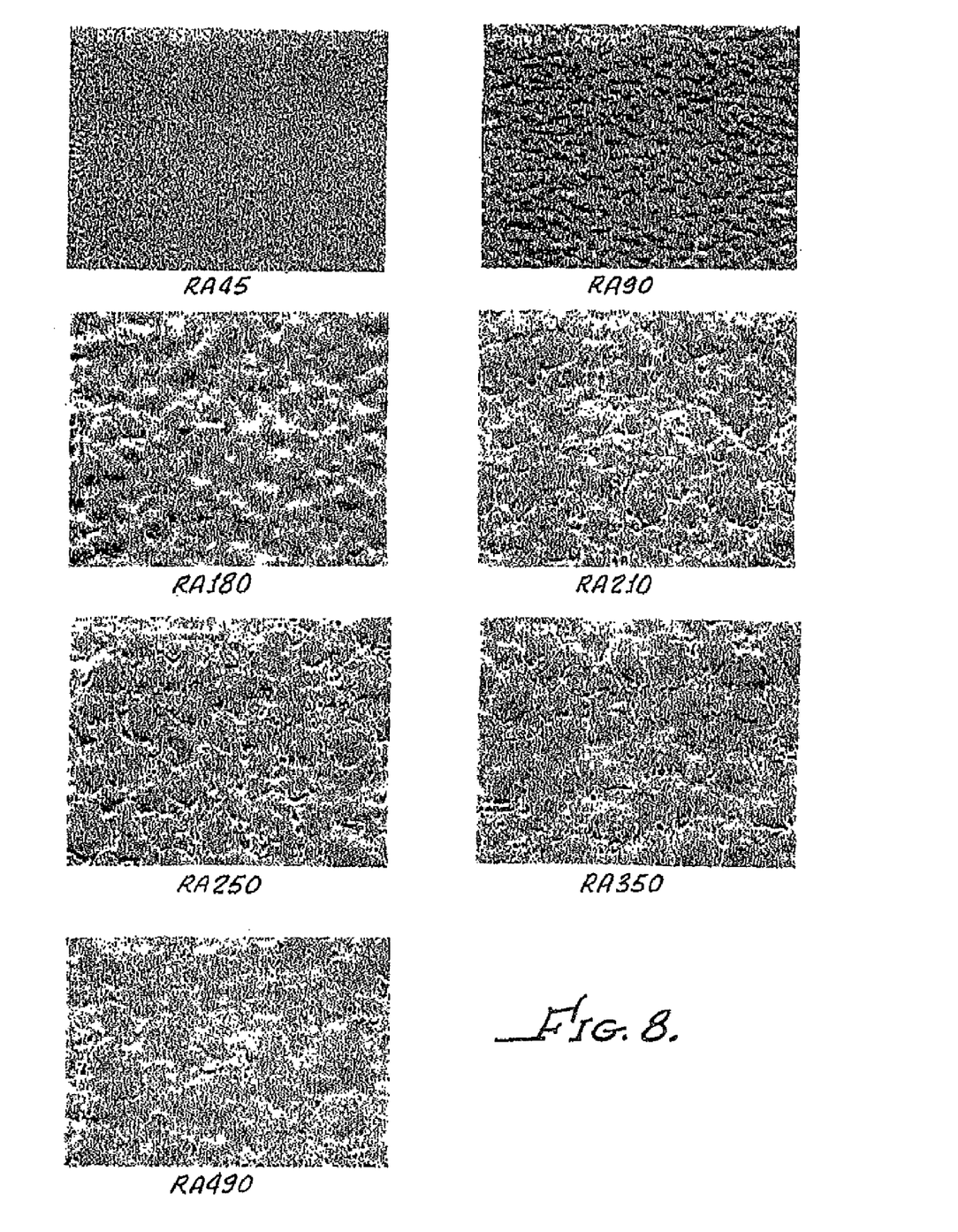
FIG. 8 are microscopic views of surface roughness on the lens shown in FIGS. 1 and 2 with arithmetic mean roughness Ra varying from Ra 45 to Ra 490.

FIG. 8 shows magnified photographs of surfaces having average surface roughness levels, or topographies, from Ra 45 to Ra 490 and programs similar to that shown in Table 1 may be utilized for the production of the surfaces.

EXAMPLE

Six IOL's having an edge roughness 26 from Ra 45 to Ra 490 were subjected to scattering measurements at 35° and 55° incident light angles with the light of 514 nm and 633 nm, respectively.

TABLE 1

MACHINING PROGRAM FOR Ra 180 ROUGHENING ON SILICONE

```
";"
"     (****************************************************);"
"            (AMO SPARE TIRE TO A 180.+−15 RA FINISH 1/22/2003);"
"     (****************************************************);"
"            (2003/01/23 VERSION 8.2 CLRFLXB Column with bottom);"
"     (****************************************************);"
"            (2003/01/24, VERSION 8.2 SPARETIR Column with bottom);"
";"
"(     PL ON OFF IP SV S UP DN JS LNS STEP V HP PP C ALV OC LF JM LS LNM);"
"C005 = + 0040 0065 004.4 055 02 008 40 010 0001 0.00000 02 000 00 0 0018 0015 0000 01 02 303;"
"C006 = + 0020 0030 003.0 060 02 008 040 010 0001 0.00000 02 000 10 0 0018 0013 0000 01 03 303;"
"C029 = + 0016 0025 002.4 060 02 008 040 010 0001 0.00000 02 000 10 0 0012 0013 0000 01 03 303;"
";"
"H005       = + 00000.00013    (123:RGH.S-FIN.FIN,1:RGH,13:RGH.FIN,    );"
"                              (12:RGH.S-FIN,2:S-FIN,23:S-FIN.FIN,3:FIN );"
"H017       = + 00000.00000    (1:COMBINATION                          );"
"H002       = − 00000.01830    (MACHINING DEPTH                        );"
"H011       = + 00000.00555    (EL1 UNDER SIZE                         );"
"H012       = + 00000.00555    (EL2 UNDER SIZE                         );"
"H013       = + 00000.00555    (EL3 UNDER SIZE                         );"
"H027       = + 00000.02500    (COLLISION AVOIDANCE POSITION           );"
"H010       = + 00000.00003    (EL PROCESS NO.                         );"
"H028       = + 00000.00158    (SIDE OFFSET                            );"
"H030       = + 00000.00252    (BOTTOM OFFSET                          );"
"H048       = + 00000.00004    (CONDITION COUNT                        );"
"H018       = + 00000.00303    (LNM                                    );"
"H019       = + 00000.00001    (LNS                                    );"
"H000       = + 00000.10000    (Projected area                         );"
"H003       = + 00000.01250    (ACTUAL DEPTH                           );"
"H008       = + 00000.50501    (CONDITION                              );"
"H009       = + 00000.00030    (TIMER                                  );"
"H001       = + 00000.00000    (MACHINING DIRECTION                    );"
"H007       = + 00000.00000    (ABS/INC                                );"
"H006       = + 00000.01401    (SIDE MACHINING AREA                    );"
"H025       = + 00000.00059    (SIDE ESCAPE                            );"
"H026       = + 00000.00079    (BOTTOM ESCAPE                          );"
"H032       = + 00000.00000    (LORAN ROTATION                         );"
";"
"G90;"
"H900=H027 H940=0 H941=0 H942=3 H950=1 H951=0 H952=0 H910=0 H947=0 H960=0;"
"G24;"
"IFH005=3(1100);"
"IFH005=23(1110);"
"IFH005=2(1110);"
"JUMP1120;"
"N1100 H942=3;"
"G83 Z920;"
"JUMP2300;"
"N1110 H942=2;"
"G83 Z920;"
"JUMP2200;"
"N1120;"
"G83 Z920;"
";"
"N2200;"
"N2300;"
"QATP(54, 1, 0, 3, 1, 0.00000, 0.00000, 1.00000, 0.00000, H027, 030);"
"CRT(- EL3-COND1-HOLE1 -);"
```

TABLE 1-continued

MACHINING PROGRAM FOR Ra 180 ROUGHENING ON SILICONE

"M98P2001;"
"QATP(54, 1, 0, 3, 1, 0.00000, 0.00000, 1.00000, 0.00000, H027, 030);"
"CRT(- EL3-COND2-HOLE1 -);"
"M98P2002;"
"QATP(54, 1, 0, 3, 1, 0.00000, 0.00000, 1.00000, 0.00000, H027, 030);"
"CRT(- EL3-COND3-HOLE1 -);"
"M98P2003;"
"QATP(54, 3, 0, 3, 2, 0.00000, 0.00000, 1.00000, 0.00000, H027, 030);"
"CRT(- EL3-COND1-HOLE2 -);"
"M98P2001;"
"QATP(54, 3, 0, 3, 2, 0.00000, 0.00000, 1.00000, 0.00000, H027, 030);"
"CRT(- EL3-COND2-HOLE2 -);"
"M98P2002;"
"QATP(54, 3, 0, 3, 2, 0.00000, 0.00000, 1.00000, 0.00000, H027, 030);"
"CRT(- EL3-COND3-HOLE2 -);"
"M98P2003;"
"QATP(54, 5, 0, 3, 3, 0.00000, 0.00000, 1.00000, 0.00000, H027, 030);"
"CRT(- EL3-COND1-HOLE3 -);"
"M98P2001;"
"QATP(54, 5, 0, 3, 3, 0.00000, 0.00000, 1.00000, 0.00000, H027, 030);"
"CRT(- EL3-COND2-HOLE3 -);"
"M98P2002;"
"QATP(54, 5, 0, 3, 3, 0.00000, 0.00000, 1.00000, 0.00000, H027, 030);"
"CRT(- EL3-COND3-HOLE3 -);"
"M98P2003;"
";"
"N2400;"
"G90 G00 M05 ZH920;"
"IF H027=99999999(2401);"
"G00 ZH027;"
"JUMP2402;"
"N2401;"
"G81 Z+;"
"N2402;"
"IF H017=1(9999);"
"IFH005=1(2410);"
"IFH005=2(2410);"
"IFH005=12(2410);"
"JUMP9999;"
"N2410;"
"CRT(EL CHANGE);"
"JUMP9999;"
";"
"N2001;"
"C005;"
"H010=3 H030 = 0.00610 H028=0.00311 H048=2 H009=10;"
"G85 TH009;"
"M98 P3300;"
"M99;"
"N2002;"
"C006;"
"H010=3 H030=0.00402 H028=0.00173 H048=3 H009=20;"
"G85 TH009;"
"M98 P3300;"
"M99;"
"N2003;"
"C029;"
"H010=3 H030=0.00252 H028=0.00158 H048=4 H009=30;"
"G85 TH009;"
"M98 P3300;"
"M99;"
";"
"(01FEB2002 V3.00 111);"
"N3100 (************* PATTERN 1 *************);"
"G83R923;"
"IF H923=2(,3110);"
"M99 (*** DELETE M99 : FULL DRY RUN ***);"
"N3110;"
"IF H002<H920(3120);"
"H030=0-H030;"
"H026=0-H026;"
"N3120;"
"M98 P3500;"
";"
"M98 P3600;"
"JUMP 3900;"
";"
"N3200 (*********** PATTERN 2 3 ***********);"

TABLE 1-continued

MACHINING PROGRAM FOR Ra 180 ROUGHENING ON SILICONE

```
"N3300;"
"G83R923;"
"IF H923=2(,3210);"
"M99 (***** DELETE M99 : FULL DRY RUN *****);"
"N3210;"
"IF H002<H920(3220);"
"H030=0-H030;"
"H026=0-H026;"
"N3220;"
"M98 P3500;"
"M98 P3600;"
"JUMP 3900;"
";"
"N3500 (******** PARAMETER IS SET UP **********);"
"G24;"
"LNMH018 LNSH019 LP0000;"
"G83UP918;"
"QALEC(H000,H003,H008,H018,H019,1);"
"N3530      ( ** WITH ROTATION ** );"
"IF H960=0(3550);"
"G83 U947;"
"LAH032+H947;"
"G326;"
"M99;"
"N3550;"
"LAH032;"
"G326;"
"M99;"
";"
"N3600 (************ MACHINING **************);"
"G90+H007;"
"IF H048<>1(3610);"
"STEP0      ( ** 1ST MACH. ** );"
"G01 Z+H002+H030 M04;"
"N3610;"
"IF H048>800(,3660);"
"N3620      ( ** TIMER MACHINING ** );"
"IF H000<10./25.4*1./25.4*1.(3660);"
"QTIMER(H000,H006,H009,0.254/1000.,0);"
"N3630 G85 ZH909 (** FOR SIDE ** );"
"STEP0+H[010+H010]-H028;"
"G01 Z+H002+H030+H026 M04;"
"N3640;"
"QTIMER(H000,H006,H009,0.254/1000.,1);"
"N3650 G85 ZH909 ( ** FOR BOTTOM ** );"
"STEP0+H[010+H010]-H028-H025;"
"JUMP3670;"
"N3660      ( ** FROM 2ND MACH ** );"
"STEP0;"
"IF H[010+H010]-H028<0.004/25.4*1.(3670);"
"STEP0+H[010+H010]-H028;"
"N3670;"
"G01 Z+H002+H030 M04;"
"G90;"
"M99;"
";"
"N3900 (************ READ TIME *************);"
"G327;"
"UPH918;"
"G83 T[300+H952];"
"H[301+H952]=99999;"
"IF H952>100(3999);"
"H952=H952+1;"
"M99;"
"N3999;"
"H952=0;"
"M99;"
"N9999;"
```

Figure 9:
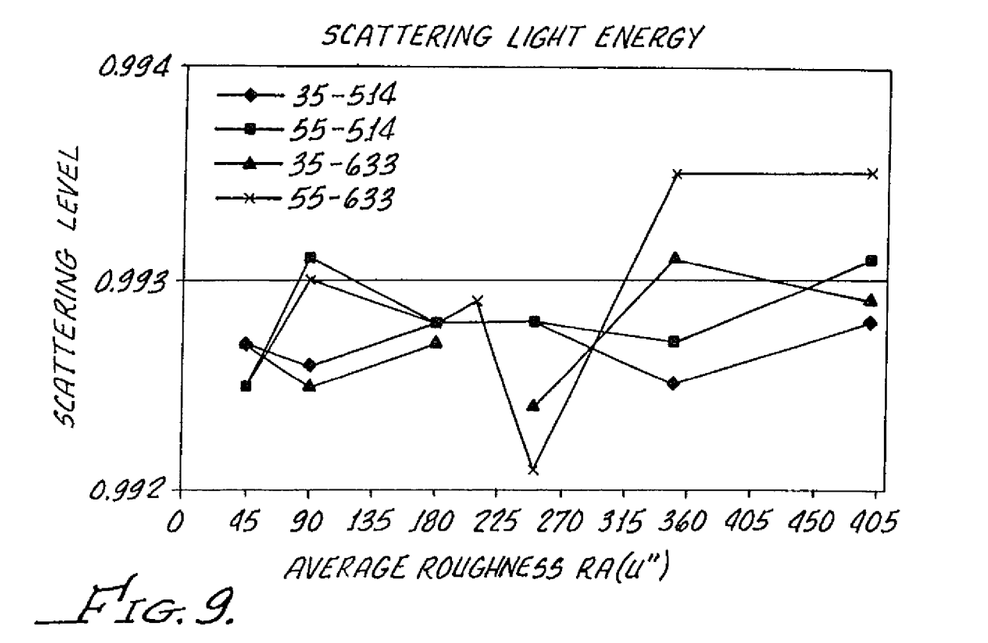
FIG. 9 are analyzed results from sample surfaces having the average roughness from Ra 45 to Ra 490 showing the scattering level as a function of roughness.

From the measured scattering results, it has been found that all surface scattering follow a Gaussian distribution by fitting the measured data to a Gaussian scattering model, as shown in FIG. 9, which is a plot of scattering level versus average roughness.

Figure 10:
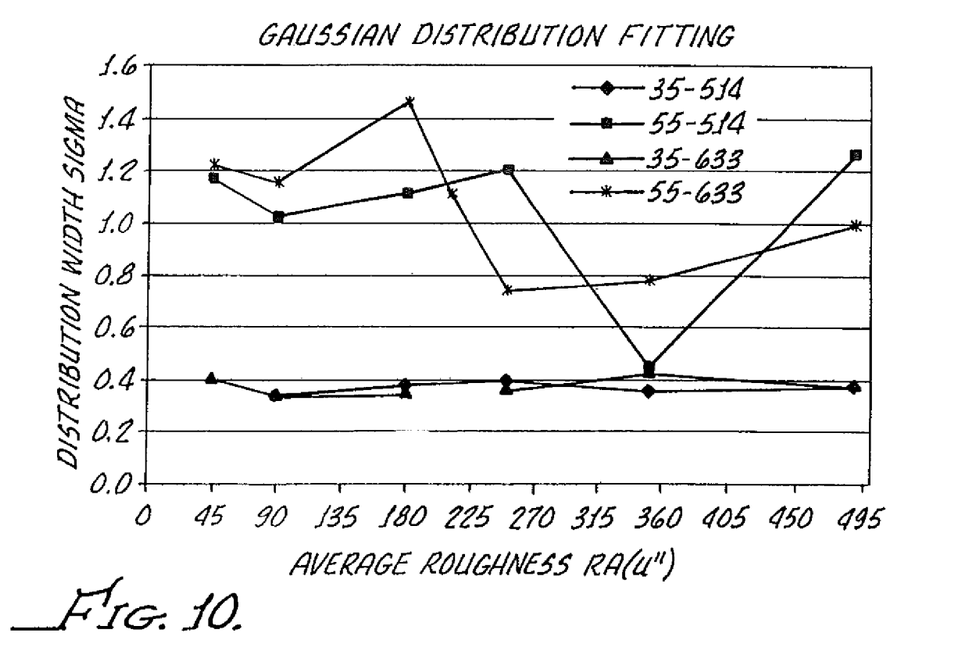
FIG. 10 is a plot of distribution width sigma as a function of surface roughness with the data fitted to a Gaussian distribution model.

Measured scattering level is about 0.993, as shown, and, as shown in FIG. 10 the distribution width sigma ranges from 0.4 to 1.5 with Ra 180 having the maximum. A fitting correlation $R^2$ values for all cases are above 0.95. Accordingly, the Ra 180 surface has found to have the best scattering ability, is closest to random scattering.

In view of variation of distribution width sigma shown in FIG. 10, this result could not be predicted on the basis of the roughness Ra value. That is, there is no predictable connection, or correlation, between Ra and scattering effectiveness.

Figure 11:
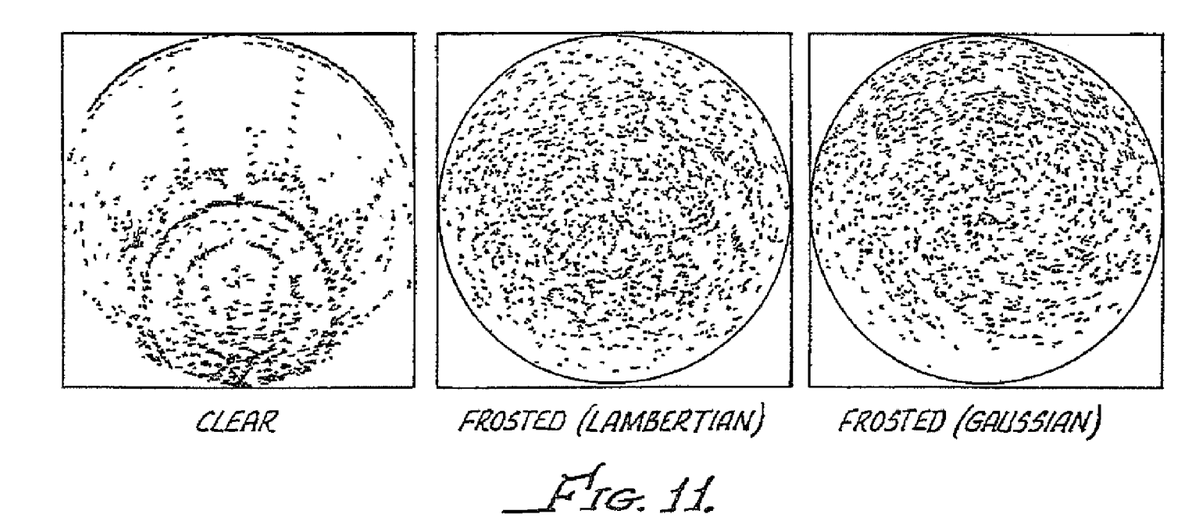
FIG. 11 is a comparison of glare at 55° incident angle for the intraocular lens made in accordance with the present invention with a roughened edge having average roughness of Ra 180 with an identical lens without edge roughening, i.e., a clear lens.

FIG. 11 shows simulated comparison examples of the scattering analysis done on the lens 10 with and without (clear) a roughness of Ra 180 at 55° incident light angle. Defrosted (Lambertian) means the peripheral anterior area 24 and slope edge 28 are frosted with a uniform (Lambertian model) scattering surface finished with 0.9 scattering level and frosted (Gaussian) means the peripheral area of the IOL interior surface 24 and the IOL slope edge 28 are frosted with a non-uniform (Gaussian model) scattering surface with 0.9 scattering level at 1.4 half distribution sigma width.

The corresponding glare pattern average intensity and local contrast of the lenses is shown in Table 2

TABLE 2

The corresponding glare pattern average intensity and local contrast of cases in FIG. 11.

| | Clariflex | Clear | Lambertian | Gaussian |
|---|---|---|---|---|
| Average Intensity | $1.04 \times 10^6$ | | $0.62 \times 10^4$ | $0.75 \times 10^4$ |
| Local Contrast | 0.88 | | 0.02 | 0.08 |

It should be apparent that the results for the frosted lenses as shown in FIG. 11 illustrate an almost a uniform contrast with no discernment of glare patterns as is evidenced with the clear lens.

Although there has been hereinabove described a specific glare reducing rough surfaces in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

The invention claimed is:

1. A process of fabricating an intraocular lens (IOL), the process comprising:
    providing a blank lens having a center lens optical portion, a surrounding lens portion, and at least one haptic coupled to the surrounding lens portion,
        wherein the center lens optical portion focuses incoming light toward the retina of an eye, and the surrounding lens portion has an anterior surface, a posterior surface, and a peripheral edge surface, said peripheral edge surface intersecting at least one of said anterior and posterior surfaces;
    roughening the peripheral edge surface such that the peripheral edge surface has a glare-reducing rough surface with a surface roughness level of about Ra 180 μ in; the rough surface having a Gaussian distribution width sigma of at least 1 when illuminated by an incident light beam, and scattering data from the illuminated rough surface is fitted to a Gaussian distribution model, the incident light beam having a wavelength of 633 nanometers and illuminating the surface at a 55 degree incident light angle; and
    wherein the center lens optical portion has no surface roughening applied thereto.

2. The process according to claim 1 wherein selected portions of the surrounding lens portion are roughened.

3. The process according to claim 1 wherein roughening the surrounding lens portion comprises roughening a selected area by Electrical Discharge Machining.

4. The process according to claim 3 wherein the roughening of the surrounding lens portion further comprises controlling the Electrical Discharge Machining through a program as set forth in Table 1.

* * * * *